US009023233B2

(12) United States Patent
Furuta et al.

(10) Patent No.: US 9,023,233 B2
(45) Date of Patent: May 5, 2015

(54) AZEOTROPIC OR AZEOTROPE-LIKE COMPOSITION, AND METHOD FOR PRODUCING 2,3,3,3-TETRAFLUOROPROPENE OR CHLOROMETHANE

(71) Applicant: Asahi Glass Company, Limited, Chiyoda-ku (JP)

(72) Inventors: Shoji Furuta, Chiyoda-ku (JP); Tetsuo Otsuka, Chiyoda-ku (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 0 days.

(21) Appl. No.: 14/498,153

(22) Filed: Sep. 26, 2014

(65) Prior Publication Data

US 2015/0008357 A1 Jan. 8, 2015

Related U.S. Application Data

(63) Continuation of application No. PCT/JP2013/060547, filed on Apr. 5, 2013.

(30) Foreign Application Priority Data

Apr. 9, 2012 (JP) ................................ 2012-088529

(51) Int. Cl.
*C09K 5/04* (2006.01)
*C07C 17/383* (2006.01)

(52) U.S. Cl.
CPC ............... *C07C 17/383* (2013.01); *C09K 5/044* (2013.01); *C09K 2205/32* (2013.01)

(58) Field of Classification Search
CPC ...... C07C 21/18; C07C 17/383; C07C 19/03; C09K 5/04
USPC ............................................ 252/67; 570/178
See application file for complete search history.

(56) References Cited

U.S. PATENT DOCUMENTS 2,931,840 A 4/1960 Marquis et al.
2005/0233923 A1 10/2005 Singh et al.
2005/0233931 A1 10/2005 Singh et al.
2005/0233932 A1 10/2005 Singh et al.
2005/0233933 A1 10/2005 Singh et al.
2005/0233934 A1 10/2005 Singh et al.
2006/0019857 A1 1/2006 Wilson et al.
2006/0022166 A1 2/2006 Wilson et al.
2006/0025322 A1 2/2006 Wilson et al.
2006/0033071 A1 2/2006 Wilson et al.
2006/0033072 A1 2/2006 Wilson et al.
2006/0043330 A1 3/2006 Wilson et al.
2006/0116310 A1 6/2006 Singh et al.
2009/0092556 A1 4/2009 Singh et al.
2009/0253946 A1 10/2009 Van Der Puy
2011/0178343 A1* 7/2011 Kruper et al. ................ 570/159
2012/0151999 A1 6/2012 Seybold et al.
2012/0204594 A1 8/2012 Singh et al.

FOREIGN PATENT DOCUMENTS

JP 2008-506793 3/2008
WO WO 2005103190 A1 * 11/2005
WO 2011/030026 3/2011
WO WO 2013 151070 A1 * 10/2013
WO WO 2013154059 A1 * 10/2013
WO WO 2014103582 A1 * 7/2014

OTHER PUBLICATIONS

International Preliminary Report, PCT/JP2013/060547, pp. 1-4, mailed Jul. 9, 2013.*
International Search Report issued in corresponding PCT/JP2013/060547, mailed Jul. 9, 2013.
U.S. Appl. No. 14/486,143, filed Sep. 15, 2014, Furuta, et al.
U.S. Appl. No. 14/486,125, filed Sep. 15, 2014, Furuta, et al.

* cited by examiner

*Primary Examiner* — Douglas McGinty
(74) *Attorney, Agent, or Firm* — Oblon, McClelland, Maier & Neustadt, L.L.P.

(57) ABSTRACT

To provide a method for efficiently separating 2,3,3,3-tetrafluoropropene (HFO-1234yf) and chloromethane (R40) from a composition comprising HFO-1234yf and R40. An azeotrope-like composition comprising from 58 to 78 mol % of HFO-1234yf and from 22 to 42 mol % of R40, and a method for producing HFO-1234yf, which comprises steps of distilling an initial mixture containing HFO-1234yf in a content exceeding 63 mol % in the total amount of HFO-1234yf and R40, thereby to separate the initial mixture into a first fraction in which the content of HFO-1234yf in the total amount of HFO-1234yf and R40 is lower than the content of HFO-1234yf in the total amount of HFO-1234yf and R40 in the initial mixture, and a second fraction in which the content of HFO-1234yf in the total amount of HFO-1234yf and R40 is higher than the content of HFO-1234yf in the total amount of HFO-1234yf and R40 in the initial mixture, and then obtaining HFO-1234yf having a reduced R40 concentration, from the second fraction.

8 Claims, No Drawings

AZEOTROPIC OR AZEOTROPE-LIKE COMPOSITION, AND METHOD FOR PRODUCING 2,3,3,3-TETRAFLUOROPROPENE OR CHLOROMETHANE

This application is a continuation of PCT Application No. PCT/JP2013/060547 filed on Apr. 5, 2013, which is based upon and claims the benefit of priority from Japanese Patent Application No. 2012-088529 filed on Apr. 9, 2012. The contents of those applications are incorporated herein by reference in their entireties.

TECHNICAL FIELD

The present invention relates to an azeotropic or azeotrope-like composition comprising 2,3,3,3-tetrafluoropropene and chloromethane, and a method for producing 2,3,3,3-tetrafluoropropene or chloromethane from a mixture of 2,3,3,3-tetrafluoropropene and chloromethane.

BACKGROUND ART

In recent years, 2,3,3,3-tetrafluoropropene (HFO-1234yf) has attracted attention as a new refrigerant to be substituted for 1,1,1,2-tetrafluoroethane (HFC-134a) which is a greenhouse gas. Here, in this specification, with respect to a halogenated hydrocarbon, in brackets after its chemical name, an abbreviated name of the compound is indicated. However, in this specification, as the case requires, instead of the chemical name, its abbreviated name is used.

As a method for the production of HFO-1234yf, for example, a method is known wherein 1,1-dichloro-2,3,3,3-tetrafluoropropene (CFO-1214ya) obtainable by dehydrofluorinating 1,1-dichloro-2,2,3,3,3-pentafluoropropane (HCFC-225ca) with an aqueous alkaline solution in the presence of a phase-transfer catalyst, is used as a raw material and is reduced by hydrogen to produce HFO-1234yf.

However, in such a method, the number of reaction steps is many, and purification by distillation of an intermediate product or the final product is required. On the other hand, a method for producing HFO-1234yf by one reaction involving thermal decomposition, from a raw material containing a chlorofluorocarbon, has been proposed. As such a method, for example, Patent Document 1 proposes a method to obtain HFO-1234yf by pyrolyzing a mixture of chloromethane (R40) and chlorodifluoromethane (R22) and/or tetrafluoroethylene (TFE).

PRIOR ART DOCUMENT

Patent Document

Patent Document 1: U.S. Pat. No. 2,931,840

DISCLOSURE OF INVENTION

Technical Problem

By a study made by the present inventors, it has been found that in a case where HFO-1234yf is produced by the above method, the obtained reaction mixture contains, in addition to the desired product HFO-1234yf, unreacted raw materials as well as byproducts, and R40 has a low reactivity than R22 and TFE and thus tends to remain in a large amount in the reaction mixture. In order to obtain the desired product HFO-1234yf in good yield from such a reaction mixture, it is desired to efficiently separate R40 as an unreacted raw material from HFO-1234yf and reuse it.

The present invention has been made from such a viewpoint and has an object to provide a method for efficiently separating 2,3,3,3-tetrafluoropropene (HFO-1234yf) and chloromethane (R40) from a composition comprising HFO-1234yf and R40.

Solution to Problem

The present invention provides an azeotropic composition comprising 63 mol % of 2,3,3,3-tetrafluoropropene and 37 mol % of chloromethane.

Further, the present invention provides an azeotrope-like composition comprising from 58 to 78 mol % of 2,3,3,3-tetrafluoropropene and from 22 to 42 mol % of chloromethane.

The present invention provides a mixed composition comprising 2,3,3,3-tetrafluoropropene and chloromethane, wherein the total amount of 2,3,3,3-tetrafluoropropene and chloromethane is at least 90 mol % in the mixed composition, and the content ratio of 2,3,3,3-tetrafluoropropene to chloromethane is 2,3,3,3-tetrafluoropropene/chloromethane=63/37 by molar ratio.

The present invention provides a mixed composition comprising 2,3,3,3-tetrafluoropropene and chloromethane, wherein the total amount of 2,3,3,3-tetrafluoropropene and chloromethane is at least 90 mol % in the mixed composition, and the content ratio of 2,3,3,3-tetrafluoropropene to chloromethane is 2,3,3,3-tetrafluoropropene/chloromethane=from 58/42 to 78/22 by molar ratio.

The present invention provides a refrigerant containing the above azeotropic composition or azeotrope-like composition of the present invention.

The present invention provides a method for producing 2,3,3,3-tetrafluoropropene, which comprises steps of distilling an initial mixture composed mainly of 2,3,3,3-tetrafluoropropene and chloromethane, wherein the content ratio of 2,3,3,3-tetrafluoropropene in the total amount of 2,3,3,3-tetrafluoropropene and chloromethane exceeds 63% by molar ratio, thereby to separate the initial mixture into a first fraction in which the content ratio of 2,3,3,3-tetrafluoropropene in the total amount of 2,3,3,3-tetrafluoropropene and chloromethane is lower than the content ratio of 2,3,3,3-tetrafluoropropene in the total amount of 2,3,3,3-tetrafluoropropene and chloromethane in the initial mixture, and a second fraction in which the content ratio of 2,3,3,3-tetrafluoropropene in the total amount of 2,3,3,3-tetrafluoropropene and chloromethane is higher than the content ratio of 2,3,3,3-tetrafluoropropene in the total amount of 2,3,3,3-tetrafluoropropene and chloromethane in the initial mixture, and then obtaining 2,3,3,3-tetrafluoropropene having a reduced chloromethane concentration, from the second fraction.

Further, the present invention provides a method for producing chloromethane, which comprises steps of distilling an initial mixture composed mainly of 2,3,3,3-tetrafluoropropene and chloromethane, wherein the content ratio of chloromethane in the total amount of 2,3,3,3-tetrafluoropropene and chloromethane exceeds 37% by molar ratio, thereby to separate the initial mixture into a first fraction in which the content ratio of chloromethane in the total amount of 2,3,3,3-tetrafluoropropene and chloromethane is lower than the content ratio of chloromethane in the total amount of 2,3,3,3-tetrafluoropropene and chloromethane in the initial mixture, and a second fraction in which the content ratio of chloromethane in the total amount of 2,3,3,3-tetrafluoropropene and chloromethane is higher than the content ratio of chloromethane in the total amount of 2,3,3,3-tetrafluoropropene and chloromethane in the initial mixture, and then obtaining chloromethane having a reduced 2,3,3,3-tetrafluoropropene concentration, from the second fraction.

Advantageous Effects of Invention

According to the present invention, it is possible to efficiently separate 2,3,3,3-tetrafluoropropene (HFO-1234yf) and chloromethane (R40) from a composition comprising HFO-1234yf and R40.

DESCRIPTION OF EMBODIMENTS

Now, embodiments of the present invention will be described.

[Azeotropic Composition]

An azeotropic composition comprising HFO-1234yf and R40 of the present invention is a composition wherein the content ratio of HFO-1234yf is 63 mol %, and the content ratio of R40 is 37 mol %, and has a boiling point of 41.3° C. under a pressure of $1.011\times10^6$ Pa. The azeotropic composition undergoes no change in its composition when repeatedly subjected to distillation and condensation and thus has such a merit that when it is used in an application to a refrigerant or the like, an extremely stable performance is obtainable. Further, the azeotropic composition has a relative volatility of 1.00 as represented by the following formula.

(Formula to Obtain Relative Volatility)

Relative volatility=(mol % of HFO-1234*yf* in gas phase/mol % of *R*40 in gas phase)/(mol % of HFO-1234*yf* in liquid phase/mol % of *R*40 in liquid phase)

[Azeotrope-Like Composition]

The azeotrope-like composition comprising HFO-1234yf and R40 of the present invention is a composition wherein the content ratio of HFO-1234yf is from 58 to 78 mol %, and the content ratio of R40 is from 22 to 42 mol %. It undergoes little change in its composition when repeatedly subjected to distillation and condensation. Here, in this specification, an azeotrope-like composition is a composition wherein the relative volatility obtained by the above formula is within a range of 1.00±0.20. Further, the azeotrope-like composition comprising HFO-1234yf and R40 of the present invention has a boiling point of from 41 to 42° C. under a pressure of $1.011\times10^6$ Pa.

The azeotrope-like composition of the present invention can be handled substantially in the same manner as the above-described azeotropic composition of the present invention and has such a merit that when it is used in an application to a refrigerant or the like, a stable performance equal to the azeotropic composition is obtainable. Further, in the following description, the azeotrope-like composition will be described as including the azeotropic composition.

[Mixed Composition]

The mixed composition in the first embodiment of the present invention is a mixed composition comprising 2,3,3,3-tetrafluoropropene and chloromethane, wherein the total amount of 2,3,3,3-tetrafluoropropene and chloromethane is at least 90 mol % in the mixed composition, and the content ratio of 2,3,3,3-tetrafluoropropene to chloromethane is 2,3,3,3-tetrafluoropropene/chloromethane=63/37 by molar ratio.

The mixed composition in the second embodiment of the present invention is a mixed composition comprising 2,3,3,3-tetrafluoropropene and chloromethane, wherein the total amount of 2,3,3,3-tetrafluoropropene and chloromethane is at least 90 mol % in the mixed composition, and the content ratio of 2,3,3,3-tetrafluoropropene to chloromethane is 2,3,3,3-tetrafluoropropene/chloromethane=from 58/42 to 78/22 by molar ratio.

The mixed composition of the present invention may contain less than 10 mol % of other components in addition to 1234yf and R40. Such other components may, for example, be hydrochiorocarbons, hydrofluorocarbons, hydrochlorofluorocarbons, chlorofluorocarbons, fluorocarbons and chlorocarbons. Specifically, R22, TFE, HFP, RC318, CTFE, trifluoroethylene, HFPO, difluoroethylene, tetrafluoroethane, trifluoropropene, difluoroethane, heptafluoropropane, chlorodifluoroethylene, chloroethylene, chlorotetrafluoroethane, chlorofluoromethane, perchloroethylene, perchloromethane and difluoromethane may be mentioned. Such other components are preferably at most 5 mol %, more preferably at most 3 mol %.

[Refrigerant]

The refrigerant of the present invention contains the azeotropic composition or azeotrope-like composition of the present invention. The content ratio of the azeotropic composition or azeotrope-like composition of the present invention in the refrigerant of the present invention is preferably at least 80 mass %, more preferably at least 90 mass %. As the refrigerant of the present invention contains the azeotropic composition or azeotrope-like composition of the present invention, it is possible to adjust the refrigerating performance of the refrigerant. The refrigerant of the present invention is particularly preferably a refrigerant consisting of the azeotropic composition or azeotrope-like composition of the present invention.

Further, the refrigerant of the present invention may contain a water-capturing agent, an acid-capturing agent, an antioxidant and a stabilizer, as the case requires. Further, the refrigerant of the present invention can be used in combination with a lubricant oil to be used typically for freezing and air-conditioning systems, which contains a polyalkylene glycol (PAG), a polyol ester (POE), a polyvinyl ether (PVE), an alkylbenzene, a synthetic paraffin, a synthetic naphthene or a poly(α-)olefin.

[Method for Producing HFO-1234yf or R40]

The present invention provides a method for producing highly purified HFO-1234yf or highly purified R40, by utilizing a step of distilling the initial mixture composed mainly of HFO-1234yf and R40, depending upon the content ratios of HFO-1234yf and R40 in the total amount of HFO-1234yf and R40 in the initial mixture.

In the method of the present invention, the content ratios of HFO-1234yf and R40 in the initial mixture may be any content ratios except for the above-mentioned content ratios at which HFO-1234yf and R40 form an azeotropic composition. Further, the initial mixture is preferably one wherein the total content of HFO-1234yf and R40 in the initial mixture is at least 90 mass %, more preferably at least 95%.

Here, in a case where the content ratio of HFO-1234yf in the total amount of HFO-1234yf and R40 in the initial mixture exceeds 63%, it is possible to produce highly purified HFO-1234yf from the initial mixture. Hereinafter, this method will be referred to as the method in the first embodiment of the present invention. In the method in the first embodiment, the content ratio of HFO-1234yf in the total amount of HFO-1234yf and R40 in the initial mixture is not particularly limited, so long as it exceeds 63% and less than 100% by molar ratio.

Whereas, in a case where the content ratio of R40 in the total amount of HFO-1234yf and R40 in the initial mixture exceeds 37%, it is possible to produce highly purified R40 from the initial mixture. Hereinafter, this method will be referred to as the method in the second embodiment of the present invention. In the method in the second embodiment, the content ratio of R40 in the total amount of HFO-1234yf and R40 in the initial mixture is not particularly limited, so long as it exceeds 37% and less than 100% by molar ratio.

The initial mixture in the method in the first embodiment or in the method in the second embodiment of the present invention, is obtainable specifically by separating a fraction consisting of a mixture of HFO-1234yf and R40, or a fraction containing such a mixture as the main component, by e.g. distillation, from a reaction mixture obtained by a method for preparing HFO-1234yf involving thermal decomposition of R40 and a fluorinated compound capable of generating $F_2C$: by thermal decomposition, such as R22, TFE, hexafluoropropene (HFP), octafluorocyclobutane (RC318), chlorotrifluoroethylene (CTFE), trifluoroethylene, hexafluoropropylene oxide (HFPO) or the like.

Here, in a case where the above fraction obtainable by the method for preparing HFO-1234yf, is to be used as the initial mixture to be supplied to the distillation step in the method of the present invention, it is not necessarily required that components other than HFO-1234yf and R40 are completely removed. That is, the fraction (the initial mixture) may contain compounds other than HFO-1234yf and R40 within a range not to impair the effects of the present invention. Specifically, it may contain R22, TFE, HFP, RC318, CTFE, trifluoroethylene, HFPO, difluoroethylene, tetrafluoroethane, trifluoropropene, difluoroethane, heptafluoropropane, chlorodifluoroethylene, chloroethylene, chlorotetrafluoroethane, chlorofluoromethane, difluoromethane, etc. The content of such other compounds is preferably less than 10 mol % in the initial mixture.

The method in the first embodiment of the present invention comprises steps of distilling an initial mixture composed mainly of HFO-1234yf and R40, wherein the content ratio of HFO-1234yf in the total amount of HFO-1234yf and R40 exceeds 63% by molar ratio, thereby to separate the initial mixture into a first fraction in which the content ratio of HFO-1234yf in the total amount of HFO-1234yf and R40 is lower than the content ratio of HFO-1234yf in the total amount of HFO-1234yf and R40 in the initial mixture, and a second fraction in which the content ratio of HFO-1234yf in the total amount of HFO-1234yf and R40 is higher than the content ratio of HFO-1234yf in the total amount of HFO-1234yf and R40 in the initial mixture, and then obtaining HFO-1234yf having a reduced R40 concentration, from the second fraction.

The distillation conditions in the first embodiment are not particularly limited, so long as they are conditions under which the initial mixture can be separated into a first fraction in which the content ratio of HFO-1234yf in the total amount of HFO-1234yf and R40 is lower than the content ratio of HFO-1234yf in the total amount of HFO-1234yf and R40 in the initial mixture, and a second fraction in which the content ratio of HFO-1234yf in the total amount of HFO-1234yf and R40 is higher than the content ratio of HFO-1234yf in the total amount of HFO-1234yf and R40 in the initial mixture. The distillation tower to be used may be a hollow distillation tower or a multi-stage distillation tower. The distillation may be carried out in a batch system or in a continuous system. The pressure condition for the distillation is preferably adjusted to be from the atmospheric pressure to 5 MPa. The temperature condition is preferably adjusted to be from −30 to 70° C. as the tower top temperature.

In a case where the distillation in the method in the first embodiment is to be carried out by means of a multi-stage distillation tower, it is common that that the initial mixture is supplied to an intermediate stage in the distillation tower, so that the first fraction in which the content ratio of HFO-1234yf in the total amount of HFO-1234yf and R40 is lower than the content ratio of HFO-1234yf in the total amount of HFO-1234yf and R40 in the initial mixture, is obtainable as a distillate from the top of the distillation tower, and the second fraction in which the content ratio of HFO-1234yf in the total amount of HFO-1234yf and R40 is higher than the content ratio of HFO-1234yf in the total amount of HFO-1234yf and R40 in the initial mixture is obtainable as a bottom product from the tower bottom.

As mentioned above, this is due to that the boiling point of the azeotrope-like composition of HFO-1234yf and R40 under a pressure of $1.011\times10^6$ Pa is from 41 to 42° C., while the boiling point of HFO-1234yf is 43° C. The first fraction in which the content ratio of HFO-1234yf in the total amount of HFO-1234yf and R40 is lower than the content ratio of HFO-1234yf in the total amount of HFO-1234yf and R40 in the initial mixture, obtainable as a distillate from the tower top, is obtainable usually as a mixed composition containing an azeotrope-like composition of HFO-1234yf and R40. By subjecting such a first fraction further to distillation repeatedly as the case requires, it is also possible to finally obtain an azeotropic composition of HFO-1234yf and R40.

Further, in such a case, the second fraction in which the content ratio of HFO-1234yf in the total amount of HFO-1234yf and R40 is higher than the content ratio of HFO-1234yf in the total amount of HFO-1234yf and R40 in the initial mixture, obtainable as the bottom product from the tower bottom, can be made to be highly pure HFO-1234yf having a low R40 concentration, by further repeating distillation as the case requires.

The highly pure HFO-1234yf thus obtainable by the method in the first embodiment of the present invention, is expected to be useful as a refrigerant.

The method in the second embodiment of the present invention comprises steps of distilling an initial mixture composed mainly of HFO-1234yf and R40, wherein the content ratio of R40 in the total amount of HFO-1234yf and R40 exceeds 37% by molar ratio, thereby to separate the initial mixture into a first fraction in which the content ratio of R40 in the total amount of HFO-1234yf and R40 is lower than the content ratio of R40 in the total amount of HFO-1234yf and R40 in the initial mixture, and a second fraction in which the content ratio of R40 in the total amount of HFO-1234yf and R40 is higher than the content ratio of R40 in the total amount of HFO-1234yf and R40 in the initial mixture, and then obtaining R40 having a reduced HFO-1234yf concentration, from the second fraction.

The distillation conditions in the second embodiment are not particularly limited, so long as they are conditions under which the initial mixture can be separated into a first fraction in which the content ratio of R40 in the total amount of HFO-1234yf and R40 is lower than the content ratio of R40 in the total amount of HFO-1234yf and R40 in the initial mixture, and a second fraction in which the content ratio of R40 in the total amount of HFO-1234yf and R40 is higher than the content ratio of R40 in the total amount of HFO-1234yf and R40 in the initial mixture. The distillation tower to be used may be a hollow distillation tower or a multi-stage distillation tower. The distillation may be carried out in a batch system or in a continuous system. The pressure condition for the distillation is preferably adjusted to be from the atmospheric pressure to 5 MPa. The temperature condition is preferably adjusted to be from −30 to 70° C. as the tower top temperature.

In a case where the distillation in the method in the second embodiment is to be carried out by means of a multi-stage distillation tower, it is common that that the initial mixture is supplied to an intermediate stage in the distillation tower, so that the first fraction in which the content ratio of R40 in the total amount of HFO-1234yf and R40 is lower than the content ratio of R40 in the total amount of HFO-1234yf and R40 in the initial mixture, is obtainable as a distillate from the top of the distillation tower, and the second fraction in which the content ratio of R40 in the total amount of HFO-1234yf and R40 is higher than the content ratio of R40 in the total amount of HFO-1234yf and R40 in the initial mixture, is obtainable as a bottom product from the tower bottom.

As mentioned above, this is due to that the boiling point of the azeotrope-like composition of HFO-1234yf and R40 under a pressure of $1.011\times10^6$ Pa is from 41 to 42° C., while the boiling point of R40 is 46° C. The first fraction in which the content ratio of R40 in the total amount of HFO-1234yf and R40 is lower than the content ratio of R40 in the total amount of HFO-1234yf and R40 in the initial mixture, obtainable as a distillate from the tower top, is obtainable usually as a mixed composition containing an azeotrope-like composition of HFO-1234yf and R40. By subjecting such a first fraction further to distillation repeatedly as the case requires, it is also possible to finally obtain an azeotropic composition of HFO-1234yf and R40.

Further, in such a case, the second fraction in which the content ratio of R40 in the total amount of HFO-1234yf and R40 is higher than the content ratio of R40 in the total amount of HFO-1234yf and R40 in the initial mixture, obtainable as the bottom product from the tower bottom, can be made to be highly pure R40 having a low HFO-1234yf concentration, by further repeating distillation as the case requires.

The highly pure R40 thus obtainable by the method in the second embodiment of the present invention, is useful, for example, as raw material R40 in the above-mentioned method for preparing HFO-1234yf involving thermal decomposition of R40 and R22 and/or TFE.

EXAMPLES

Now, the present invention will be described in detail with reference to Examples, but it should be understood that the present invention is by no means thereby restricted.

<Measurement of Gas-Liquid Equilibrium>

Each of mixtures 1 to 6 obtained by mixing HFO-1234yf and R40 in the mass ratios as shown in Table 1, was put in a 500 mL autoclave equipped with a pressure meter and gradually heated by an external heater so that the pressure would be $1.011\times10^6$ Pa. After the pressure in the autoclave reached the prescribed $1.011\times10^6$ Pa, it was maintained for a certain time to stabilize the composition in the autoclave. A sample of each of mixtures 1 to 6 was taken from the gas phase and the liquid phase, and HFO-1234yf and R40 were analyzed by gas chromatography to measure the compositional ratios of the two. From the compositional ratios of the two, the relative volatility was obtained by the above-described formula to obtain a relative volatility.

In Table 1, the compositions of the gas phase and the liquid phase, and the relative volatility, of each of mixtures 1 to 6, are shown. When the ratio of R40 in the mixture put into the autoclave was increased little by little as in mixtures 1 to 6, the value of the relative volatility gradually increased as shown in Table 1. In the case of mixture 3, the compositions of the gas phase and the liquid phase became equal with HFO-1234yf being 63 mol % and R40 being 37 mol %. At that time, the gas phase temperature was 41.3° C., and the value of the relative volatility became 1.00. When the ratio of R40 was further increased, the relative volatility increased to a value of higher than 1.00.

Although not shown in Table 1, the composition of HFO-1234yf and R40 whereby the relative volatility would be within a range of 1.00±0.20, was obtained by measuring mol % of HFO-1234yf and R40 in the gas phase and the liquid phase while gradually changing the composition of HFO-1234yf and R40 in the same manner as described above. The result was such that in the case of compositions in which the content ratio of HFO-1234yf to R40 was from 58 to 78 mol %:from 22 to 42 mol %, the relative volatility was 1.00±0.20, when the pressure was $1.011\times10^6$ Pa.

TABLE 1

| | Charged amounts [g] | | Gas phase (mol %) | | Liquid phase (mol %) | | |
|---|---|---|---|---|---|---|---|
| Mixture | R40 | HFO-1234yf | R40 | HFO-1234yf | R40 | HFO-1234yf | Relative volatility |
| 1 | 10 | 206 | 10 | 90 | 8 | 92 | 0.78 |
| 2 | 28 | 186 | 22 | 78 | 21 | 79 | 0.94 |
| 3 | 44 | 149 | 37 | 63 | 37 | 63 | 1.00 |
| 4 | 63 | 143 | 42 | 58 | 46 | 54 | 1.18 |
| 5 | 112 | 85 | 66 | 34 | 74 | 26 | 1.47 |
| 6 | 151 | 38 | 84 | 16 | 91 | 9 | 1.93 |

Example 1

As an initial mixture, initial mixture A is prepared which comprises HFO-1234yf and R40 and which comprises 75 mol % of HFO-1234yf and 25 mol % of R40 in the entire amount of the mixture. This initial mixture A is supplied to a distillation tower having a height of 2 m and an inner diameter of 4.5 cm at a rate of 300 g/hr and subjected to distillation continuously under an operation pressure of 0.5 MPa at a tower top temperature of 19° C. From the tower top, a distillate is withdrawn at a rate of 198 g/hr, and from the tower bottom, the bottom product is withdrawn at a rate of 102 g/hr. With respect to each of the distillate and the bottom product withdrawn, the composition is analyzed by gas chromatography. The analytical results of the compositions of the distillate and the bottom product are shown by mol % in the following Table 2.

As shown in Table 2, it is evident that when distillation is carried out by using as an initial mixture, a mixture wherein the content ratio of HFO-1234yf in the total amount of HFO-1234yf and R40 exceeds 63% by molar ratio, it is possible to obtain, from the tower top, an azeotrope-like composition of HFO-1234yf and R40 wherein the R40 concentration is higher and the HFO-1234yf concentration is lower than in the initial mixture, and to obtain, from the tower bottom, highly pure HFO-1234yf wherein the R40 concentration is lower than in the initial mixture.

Example 2

As an initial mixture, initial mixture B is prepared which comprises HFO-1234yf and R40 and which comprises 25 mol % of HFO-1234yf and 75 mol % of R40 in the entire amount of the mixture. This initial mixture B is supplied to a distillation tower having a height of 2 m and an inner diameter of 4.5 cm at a rate of 300 g/hr and subjected to distillation continuously under an operation pressure of 0.5 MPa at a tower top temperature of 19° C. From the tower top, a distillate is withdrawn at a rate of 163 g/hr, and from the tower bottom, the bottom product is withdrawn at a rate of 137 g/hr. With respect to each of the distillate and the bottom product withdrawn, the composition is analyzed by gas chromatography. The analytical results of the compositions of the distillate and the bottom product are shown by mol % in the following Table 2.

As shown in Table 2, it is evident that when distillation is carried out by using as an initial mixture, a mixture wherein the content ratio of R40 in the total amount of HFO-1234yf and R40 exceeds 37% by molar ratio, it is possible to obtain, from the tower top, an azeotrope-like composition of HFO-1234yf and R40 wherein the HFO-1234yf concentration is higher and the R40 concentration is lower than in the initial mixture, and to obtain, from the tower bottom, highly pure R40 wherein the HFO-1234yf concentration is low.

TABLE 2

| | Example 1 | | | Example 2 | | |
|---|---|---|---|---|---|---|
| | Composition of initial mixture A (mol %) | Composition of distillate (mol %) | Composition of bottom product (mol %) | Composition of initial mixture B (mol %) | Composition of distillate (mol %) | Composition of bottom product (mol %) |
| HFO-1234yf | 75 | 64.6 | 100 | 25 | 62.8 | N.D. |
| R40 | 25 | 35.4 | N.D. | 75 | 37.2 | 100 |

INDUSTRIAL APPLICABILITY

The azeotropic composition and the azeotrope-like composition of the present invention are useful as refrigerants. Further, according to the present invention, it is possible to efficiently separate 2,3,3,3-tetrafluoropropene (HFO-1234yf) and chloromethane (R40) from a composition comprising HFO-1234yf and R40.

What is claimed is:

1. An azeotropic composition comprising 63 mol % of 2,3,3,3-tetrafluoropropene and 37 mol % of chloromethane.

2. An azeotrope-like composition comprising from 58 to 78 mol % of 2,3,3,3-tetrafluoropropene and from 22 to 42 mol % of chloromethane.

3. A mixed composition comprising 2,3,3,3-tetrafluoropropene and chloromethane, wherein the total amount of 2,3,3,3-tetrafluoropropene and chloromethane is at least 90 mol % in the mixed composition, and the content ratio of 2,3,3,3-tetrafluoropropene to chloromethane is 2,3,3,3-tetrafluoropropene/chloromethane=63/37 by molar ratio.

4. A mixed composition comprising 2,3,3,3-tetrafluoropropene and chloromethane, wherein the total amount of 2,3,3,3-tetrafluoropropene and chloromethane is at least 90 mol % in the mixed composition, and the content ratio of 2,3,3,3-tetrafluoropropene to chloromethane is 2,3,3,3-tetrafluoropropene/chloromethane=from 58/42 to 78/22 by molar ratio.

5. A refrigerant containing the composition as defined in claim 1.

6. A refrigerant containing the composition as defined in claim 2.

7. A method for producing 2,3,3,3-tetrafluoropropene, which comprises steps of distilling an initial mixture composed mainly of 2,3,3,3-tetrafluoropropene and chloromethane, wherein the content ratio of 2,3,3,3-tetrafluoropropene in the total amount of 2,3,3,3-tetrafluoropropene and chloromethane exceeds 63% by molar ratio, thereby to separate the initial mixture into a first fraction in which the content ratio of 2,3,3,3-tetrafluoropropene in the total amount of 2,3,3,3-tetrafluoropropene and chloromethane is lower than the content ratio of 2,3,3,3-tetrafluoropropene in the total amount of 2,3,3,3-tetrafluoropropene and chloromethane in the initial mixture, and a second fraction in which the content ratio of 2,3,3,3-tetrafluoropropene in the total amount of 2,3,3,3-tetrafluoropropene and chloromethane is higher than the content ratio of 2,3,3,3-tetrafluoropropene in the total amount of 2,3,3,3-tetrafluoropropene and chloromethane in the initial mixture, and then obtaining 2,3,3,3-tetrafluoropropene having a reduced chloromethane concentration, from the second fraction.

8. A method for producing chloromethane, which comprises steps of distilling an initial mixture composed mainly of 2,3,3,3-tetrafluoropropene and chloromethane, wherein the content ratio of chloromethane in the total amount of 2,3,3,3-tetrafluoropropene and chloromethane exceeds 37% by molar ratio, thereby to separate the initial mixture into a first fraction in which the content ratio of chloromethane in the total amount of 2,3,3,3-tetrafluoropropene and chloromethane is lower than the content ratio of chloromethane in the total amount of 2,3,3,3-tetrafluoropropene and chloromethane in the initial mixture, and a second fraction in which the content ratio of chloromethane in the total amount of 2,3,3,3-tetrafluoropropene and chloromethane is higher than the content ratio of chloromethane in the total amount of 2,3,3,3-tetrafluoropropene and chloromethane in the initial mixture, and then obtaining chloromethane having a reduced 2,3,3,3-tetrafluoropropene concentration, from the second fraction.

* * * * *